US00PP28829P3

(12) United States Plant Patent
van den Hoogen

(10) Patent No.: US PP28,829 P3
(45) Date of Patent: Dec. 26, 2017

(54) ***MONARDA* PLANT NAMED 'ALLMOBIRD'**

(50) Latin Name: *Monarda didyma*
Varietal Denomination: Allmobird

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 70 days.

(21) Appl. No.: 14/998,863

(22) Filed: Feb. 23, 2016

(65) Prior Publication Data

US 2017/0245415 P1 Aug. 24, 2017

(51) Int. Cl.
*A01H 5/02* (2006.01)

(52) U.S. Cl.
USPC ..... Plt./455

(58) Field of Classification Search
USPC ..... Plt./455
See application file for complete search history.

(56) References Cited

PUBLICATIONS

UPOV hit on *Monarda* plant named 'Allmobird', QZ PBR 20152099, published Dec. 15, 2015.*

* cited by examiner

*Primary Examiner* — Anne Grunberg
(74) *Attorney, Agent, or Firm* — C. A. Whealy

(57) ABSTRACT

A new and distinct cultivar of *Monarda* plant named 'Allmobird', characterized by its upright plant habit; dark green-colored leaves; freely flowering habit; red purple-colored flowers; and long flowering period.

2 Drawing Sheets

Botanical designation: *Monarda didyma.*
Cultivar denomination: 'ALLMOBIRD'.

BACKGROUND OF THE INVENTION

The present invention relates to a new and distinct cultivar of *Monarda* plant, botanically known as *Monarda didyma*, typically grown as a cut flower and hereinafter referred to by the name 'Allmobird'.

The new *Monarda* plant is a product of a planned breeding program conducted by the Inventor in Cuijk, The Netherlands. The objective of the breeding program is to create new strong *Monarda* plants with attractive flowers and long flowering period.

The new *Monarda* plant originated from an open-pollination in September, 2013 of a proprietary selection of *Monarda didyma* identified as code number 13-45-1, not patented, as the female, or seed, parent with an unknown selection of *Monarda didyma*, as the male, or pollen, parent. The new *Monarda* plant was discovered and selected by the Inventor as a single flowering plant from within the progeny of the stated open-pollination grown in a controlled nursery environment in Cuijk, The Netherlands in August, 2014.

Asexual reproduction of the new *Monarda* plant by cuttings in Cuijk, The Netherlands, since February, 2015 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Allmobird'. These characteristics in combination distinguish 'Allmobird' as a new and distinct *Monarda* plant:

1. Upright plant habit.
2. Dark green-colored leaves.
3. Freely flowering habit.
4. Red purple-colored flowers.
5. Long flowering period.

Plants of the new *Monarda* differ primarily from plants of the female parent selection in the following characteristics:

1. Plants of the new *Monarda* have darker green-colored leaves than plants of the female parent selection.
2. Plants of the new *Monarda* and the female parent selection differ in flower color as plants of the female parent selection have purple pink-colored flowers.

Plants of the new *Monarda* can be compared to plants of *Monarda didyma* 'Saxon Purple', not patented. In side-by-side comparisons plants of the new *Monarda* differ from plants of 'Saxon Purple' in the following characteristics:

1. Plants of the new *Monarda* have dark green-colored leaves whereas plants of 'Saxon Purple' have dark green-colored leaves that are tinged with purple.
2. Plants of the new *Monarda* and 'Saxon Purple' differ in flower color as plants of 'Saxon Purple' have bluish purple-colored flowers.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical flowering plant of 'Allmobird'.

The photograph at the top of the second sheet is a close-up view of typical inflorescences of 'Allmobird'.

The photograph at the bottom of the second sheet is a close-up view of the upper surface of a typical leaf of 'Allmobird'.

DETAILED BOTANICAL DESCRIPTION

The aforementioned photographs and following observations, measurements and values describe plants grown during August in ground beds in an outdoor nursery in Rijswijk, The Netherlands and under cultural practices typical of commercial *Monarda* production. During the production of the plants, day temperatures ranged from 16° C. to 30° C. and night temperatures ranged from 8° C. to 18° C. Plants were 18 months old when the photographs and the description were taken. In the detailed description, color references are made to The Royal Horticultural Society Colour Chart, 2015 Edition, except where general terms of ordinary dictionary significance are used.

Botanical classification: *Monarda didyma* 'Allmobird'.

Parentage:

*Female, or seed, parent*.—Proprietary selection of *Monarda didyma* identified as code number 13-45-1, not patented.

*Male, or pollen, parent*.—Unknown selection of *Monarda didyma*, not patented.

Propagation:

*Type cutting*.—By cuttings.

*Time to initiate roots, summer*.—About 10 to 14 days at temperatures ranging from 12° C. to 30° C.

*Time to produce a rooted young plant, summer*.—About four to six weeks at temperatures ranging from 12° C. to 30° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; upright plant form; moderately vigorous growth habit.

*Plant height*.—About 49.6 cm.

*Plant width*.—About 43.9 cm.

*Lateral branch description*.—Branching habit: Freely basal branching habit with about five main stems, each main stem with about eight lateral branches. Length: About 22.1 cm. Diameter: About 2 mm. Internode length: About 7.1 cm. Strength: Strong. Aspect: Mostly upright. Texture and luster: Sparsely to moderately pubescent; very slightly glossy. Color: Close to 144A.

Leaf description:

*Arrangement*.—Opposite, simple.

*Length*.—About 7.5 cm.

*Width*.—About 4.2 cm.

*Shape*.—Ovate.

*Apex*.—Apiculate.

*Base*.—Cordate to obtuse.

*Margin*.—Serrate.

*Texture and luster, upper surface*.—Moderately pubescent; slightly glossy.

*Texture and luster, lower surface*.—Moderately pubescent; very slightly glossy to matte.

*Venation pattern*.—Pinnate.

*Fragrance*.—Moderately fragrant; pleasant, spicy.

*Color*.—Developing leaves, upper surface: Close to between 143B and 144A. Developing leaves, lower surface: Close to between 143C and 144B. Fully expanded leaves, upper surface: Close to NN137A; venation, close to N148A. Fully expanded leaves, lower surface: Close to 137B; venation, close to N148B.

*Petioles*.—Length: About 1.7 cm. Diameter: About 1.5 mm. Color, upper surface: Close to 144B tinged with close to 174B and 174C. Color, lower surface: Close to 144B.

Flower description:

*Flower form, arrangement and flowering habit*.—Single labiate flowers arranged in terminal globular spikes; flowers face outwardly; freely flowering habit with about 100 flowers developing per inflorescence and about 4,000 flowers developing per plant during the flowering season; flowers sessile.

*Natural flowering season*.—Long flowering habit, plants flower from mid-July to mid-September in The Netherlands.

*Postproduction longevity*.—Flowers maintain good substance for about five days on the plant; flowers not persistent.

*Fragrance*.—Moderately fragrant; pleasant, spicy.

*Flower buds*.—Length: About 1.6 cm. Diameter: About 2 mm. Shape: Narrowly oblanceolate; curved. Color: Close to 60A; towards the apex, close to 59A; immature calyx, close to between 46A and N186C.

*Inflorescence height*.—About 5.7 cm.

*Inflorescence diameter*.—About 5.4 cm.

*Flower length* (*vertical*).—About 1.5 cm.

*Flower diameter* (*horizontal*).—About 6 mm.

*Flower depth* (*height*).—About 3.2 cm.

*Petals*.—Arrangement: Labiate; upper lip hooded; lower lip, a single lobe; lips fused 60% of total length. Length, upper and lower lips: About 2.9 cm. Width, upper lip: About 2 mm. Width, lower lip: About 6 mm. Shape, upper lip: Lanceolate; apex, emarginate. Shape, lower lip: Oblanceolate; apex, caudate, cleft. Margin, upper and lower lips: Entire; lower petal, undulate. Texture and luster, upper and lower lips, upper and lower surfaces: Moderately pubescent; dull, matte. Color, upper lip: When opening and fully opened, upper surface: Close to 59D. When opening and fully opened, lower surface: Close to between 59C and 60B; color does not fade with development. Color, lower lip: When opening and fully opened, upper surface: Close to 60D. When opening and fully opened, lower surface: Close to 60C to 60D; color does not fade with development.

*Sepals*.—Quantity and arrangement: Five in a single whorl; lower 88% fused into a tubular calyx. Length: About 9 mm. Width: About 1 mm. Apex: Narrowly acute. Margin: Free parts, entire. Texture, upper and lower surfaces: Pubescent. Color: When opening, upper surface: Close to 177C. When opening, lower surface: Close to between 46A and N186C. Fully opened, upper surface: Close to 177C to 177D. Fully opened, lower surface: Close to 183B.

*Inflorescence bracts*.—Quantity and arrangement: About 16 at the base of inflorescence. Length: About 2.8 cm. Width: About 1.4 cm. Shape: Ovate to narrowly ovate; apex, acute. Margin: Entire. Texture, upper and lower surfaces: Pubescent. Color: When opening and fully opened, upper surface: Close to 178A; towards the center, close to 182A. When opening and fully opened, lower surface: Close to 147B; venation, close to 181B to 181C.

*Reproductive organs*.—Stamens: Quantity per flower: Two. Filament length: About 9 mm. Filament color: Close to 70C. Anther length: About 1.5 mm. Anther shape: Narrowly elliptic. Anther color: Close to 70A to 70B. Pollen amount: Scarce to moderate. Pollen color: Close to 11B. Pistils: Quantity per flower: One. Pistil length: About 2.8 cm. Stigma shape: Cleft, unequal. Stigma color: Close to 61A. Style length: About 2.65 cm. Style color: Close to 70B; towards the base, close to 155A. Ovary color: Close to 145D.

*Seed and fruit*.—Seed and fruit production have not been observed on plants of the new *Monarda*.

Disease & pest resistance: Plants of the new *Monarda* not been observed to be resistant to pathogens and pests common to *Monarda* plants.

Garden performance: Plants of the new *Monarda* have exhibited good tolerance to rain, wind and high temperatures about 30° C. and to be hardy to USDA Hardiness Zone 5.

It is claimed:

1. A new and distinct *Monarda* plant named 'Allmobird' as illustrated and described.

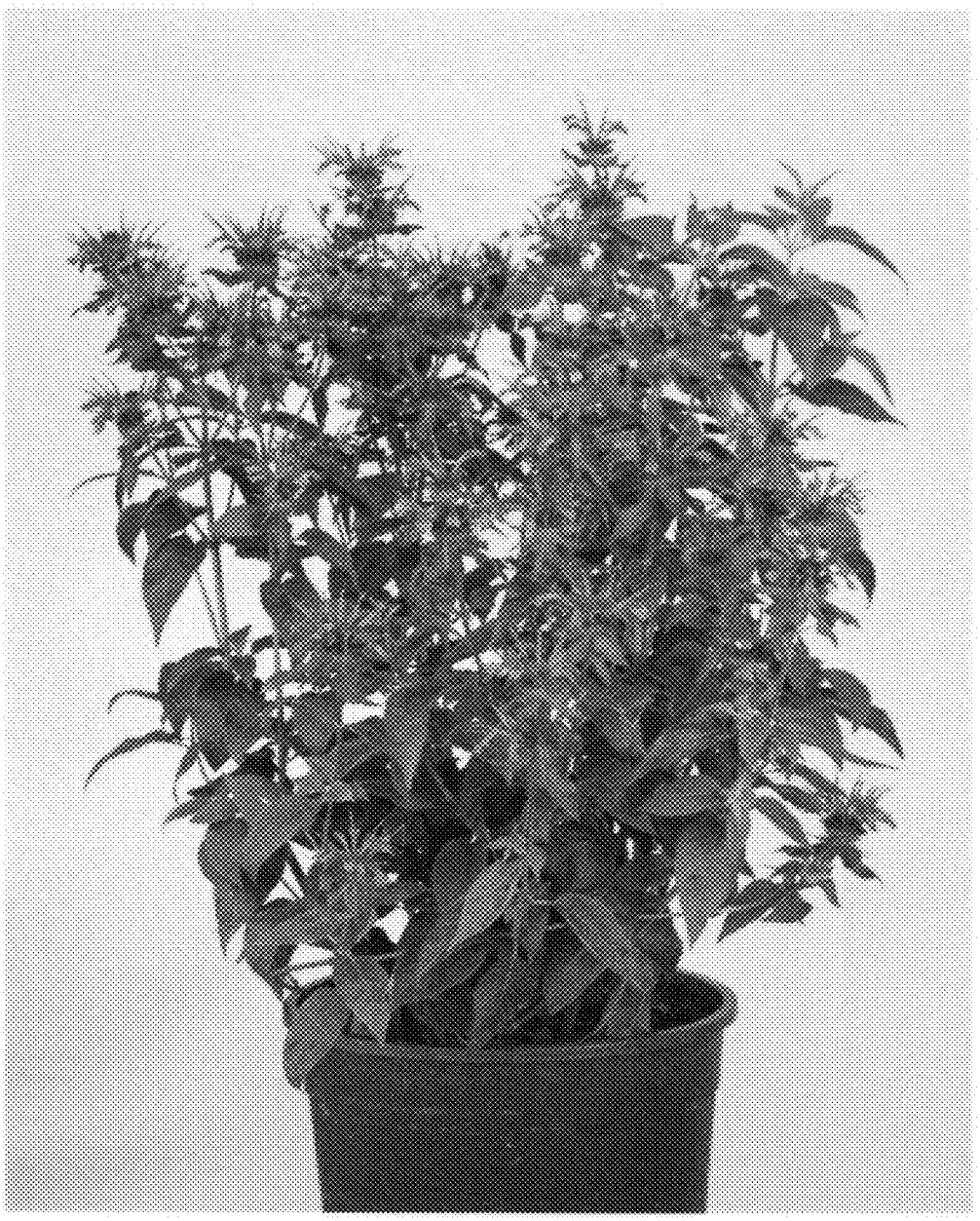

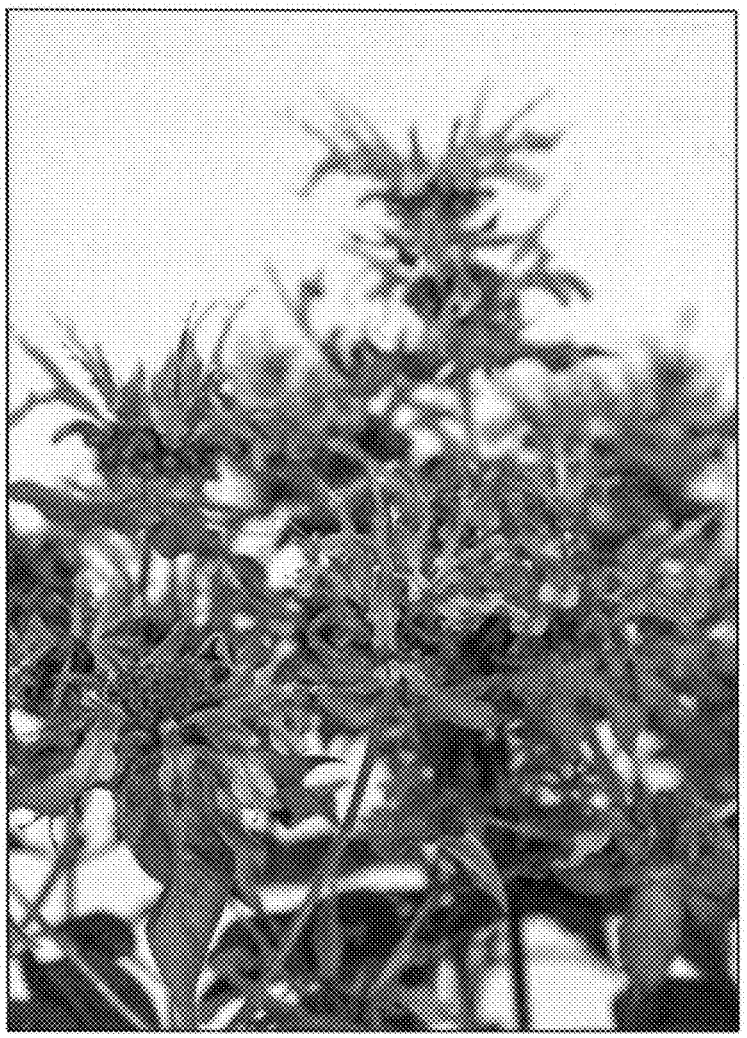
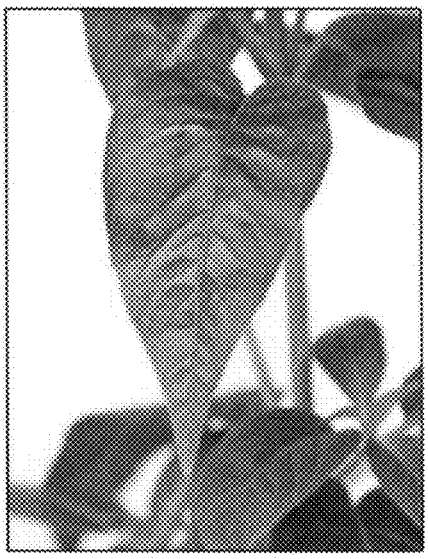

* * * * *